United States Patent
Murugesan et al.

(10) Patent No.: US 9,715,036 B2
(45) Date of Patent: Jul. 25, 2017

(54) WELLBORES INCLUDING CARBON QUANTUM DOTS, AND METHODS OF FORMING CARBON QUANTUM DOTS

(71) Applicant: Baker Hughes Incorporated, Houston, TX (US)

(72) Inventors: Sankaran Murugesan, Katy, TX (US); Othon R. Monteiro, Houston, TX (US); Valery N. Khabashesku, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 14/739,629

(22) Filed: Jun. 15, 2015

(65) Prior Publication Data
US 2016/0363693 A1    Dec. 15, 2016

(51) Int. Cl.
*G01V 8/16* (2006.01)
*C25B 1/00* (2006.01)
*G01N 21/77* (2006.01)
*G01N 21/64* (2006.01)

(52) U.S. Cl.
CPC ............... *G01V 8/16* (2013.01); *C25B 1/00* (2013.01); *G01N 21/643* (2013.01); *G01N 21/7703* (2013.01); *G01N 2021/6484* (2013.01)

(58) Field of Classification Search
CPC .................................. G01N 15/06; G01V 8/16
See application file for complete search history.

(56) References Cited

U.S. PATENT DOCUMENTS

| | | | |
|---|---|---|---|
| 7,861,601 B2 | 1/2011 | Sale et al. | |
| 2005/0111805 A1* | 5/2005 | Hertz et al. | 385/125 |
| 2011/0214488 A1* | 9/2011 | Rose et al. | 73/61.71 |
| 2012/0211365 A1* | 8/2012 | Joung et al. | 204/473 |

(Continued)

FOREIGN PATENT DOCUMENTS

| | | |
|---|---|---|
| CA | 2588862 A1 | 6/2006 |
| CA | 2410398 C | 4/2009 |

(Continued)

OTHER PUBLICATIONS

Abbaszadeh-Dehghani et al., Analysis of Well-to-Well Tracer Flow to Determine Reservoir Layering, Journal of Petroleum Technology, Oct. 1984, vol. 36, Issue 10, pp. 1753-1762.

(Continued)

*Primary Examiner* — David Porta
*Assistant Examiner* — Hugh H Maupin
(74) *Attorney, Agent, or Firm* — TraskBritt

(57) ABSTRACT

A system for determining at least one property of at least one fluid in at least one subterranean formation comprises a fluid delivery system configured and positioned to deliver a fluid into at least one of at least one subterranean formation and a wellbore extending through the at least one subterranean formation. The system comprises a radiation source within the wellbore, the radiation source configured to generate excitation radiation, carbon quantum dots disposed in the fluid, and a detector within the wellbore, the detector configured to measure at least one fluorescence property of the carbon quantum dots. Related methods of determining a property of a wellbore and methods of forming the carbon quantum dots are also disclosed.

20 Claims, 6 Drawing Sheets

(56) References Cited

U.S. PATENT DOCUMENTS

| | | | | |
|---|---|---|---|---|
| 2012/0318503 | A1* | 12/2012 | Kanj et al. | 166/252.6 |
| 2015/0218001 | A1* | 8/2015 | Wang | C09K 11/65 424/9.6 |
| 2015/0361334 | A1* | 12/2015 | Kwon et al. | |

FOREIGN PATENT DOCUMENTS

| | | |
|---|---|---|
| CN | 101973541 A | 2/2011 |
| CN | 101973541 B | 9/2012 |
| CN | 103100725 A | 5/2013 |
| CN | 103143035 A | 6/2013 |
| CN | 103143377 A | 6/2013 |
| CN | 103172051 A | 6/2013 |
| CN | 103143377 B | 11/2014 |
| CN | 103100725 B | 3/2015 |
| WO | 2004048969 A1 | 6/2004 |
| WO | 2011162939 A2 | 6/2011 |
| WO | 2013052891 A2 | 4/2013 |
| WO | 2013138622 A2 | 9/2013 |

OTHER PUBLICATIONS

Agenet et al., Fluorescent Nanobeads: a First Step Toward Intelligent Water Tracers, Society of Petroleum Engineers, SPE International Oilfield Nanotechnology Conference and Exhibition, Jun. 12-14, 2012, SPE-157019-MS, 13 pages.

Aref et al., An Improved Fiber Optic Pressure and Temperature Sensor for Downhole Application, Measurement Science and Technology, vol. 20, (2009), 7 pages.

Baker et al., Luminescent Carbon Nanodots: Emergent Nanolights, Angew. Chem. Int. Ed., vol. 49, (2010), pp. 6726-6744.

Bourlinos et al., Photoluminescent Carbogenic Dots, Chem. Mater., vol. 20, (2008), pp. 4539-4541.

Ghori et al., Well-To-Well Tracer Tests and Permeability Heterogeneity, The Journal of Canadian Petroleum Technology, vol. 37, No. 1, Jan. 1998, pp. 32-43.

Ghori et al., The Well-to-Well Tracer Tests to Determine GeostatisticalParameter of Permeability, Society of Petroleum Engineers, SPE/DOE Enhanced Oil Recovery Symposium, SPE 24138, Apr. 22-24, 1992, pp. 347-357.

Li et al., Carbon Nanodots: Synthesis, Properties and Applications, J. Mater. Chem, vol. 22, (2012), pp. 24230-24253.

Liu et al., Fluorescent Carbon Nanoparticles Derived from Candle Soot, Angew. Chem. Int. Ed., vol. 46, (2007), pp. 6473-6475.

Mahler et al., Use of Single-Well Tracer Dilution Tests to Evaluate LNAPL Flux at Seven Field Sites, Ground Water, vol. 50, No. 6, Nov.-Dec. 2012, pp. 851-860.

Raghuraman et al., Real-Time Downhole pH Measurement Using Optical Spectroscopy, Reservoir Evaluation & Engineering, Jun. 207, pp. 302-311.

Sale et al., Measurement of LNAPL Flow Using Single-Well Tracer Dilution Techniques, Ground Water, vol. 45, No. 5, Sep.-Oct. 2007, pp. 569-578.

Smith, Tim, Thesis entitled Direct Measurement of LNAPL Flow Using Single Well Periodic Mixing Reactor Tracer Tests, Department of Civil and Environmental Engineering, Colorado State4 University, 2008, 120 pages.

Sun et al., Quantum-Sized Carbon Dots for Bright and Colorful Photoluminescence, J. Am. Chem. Soc., vol. 128, 2006, pp. 7756-7757.

Tomich et al., Single-Well Tracer Method to Measure Residual Oil Saturation, Journal of Petroleum Technology, Feb. 1973, pp. 211-218.

Zhou et al., An Electrochemical Avenue to Blue Luminescent Nanocrystals from Multiwalled Carbon Nanotubes (MWCNTs), J. Am. Chem. Soc., vol. 129, 2007, pp. 744-745.

Chakraborty et al., U.S. Appl. No. 14/519,496, filed Oct. 21, 2014, and titled Suspensions for Enhanced Hydrocarbon Recovery, and Methods of Recovering Hydrocarbons Using the Suspensions.

Suresh et al., U.S. Appl. No. 14/169,432, filed Jan. 31, 2014, and titled Nano-Surfactants for Enhanced Oil Recovery, and Methods of Forming and Using Such Nano-Surfactants.

Wikipedia, Quantum Dot, http://wikipedia.or/wiki/Quantum_dot, visited May 4, 2015, 17 pages.

Princeton Instruments, Time-Resolved Fluorescence Spectroscopy, http://www.princetoninstruments.com/Uploads/Princeton/Documents/Library/UpdatedLibrary/Time_resolved_fluorescence_spectroscopy.pdf, visited May 4, 2015, 3 pages.

Turner Designs, Technical Note: An Introduction to Fluorescence Measurements, http://www.turnerdesigns.com/t2/doc/appnotes/998-0050.pdf, visited May 5, 2015,15 pages.

* cited by examiner

WELLBORES INCLUDING CARBON QUANTUM DOTS, AND METHODS OF FORMING CARBON QUANTUM DOTS

TECHNICAL FIELD

Embodiments of the disclosure relate generally to methods of forming carbon quantum dots and to methods and systems of using the carbon quantum dots to determine at least one property within subterranean formations.

BACKGROUND

During formation and operation of a wellbore, it may be desirable to measure at least one property within a subterranean formation through which the wellbore extends. For example, a high pH may be a precursor of scale build-up and a low pH may be a precursor to corrosion of wellbore equipment. Thus, the pH of a formation fluid is conventionally monitored to aid in reducing scale build-up and potential corrosion of the wellbore equipment.

Conventionally, the pH of the formation fluid is determined by obtaining a sample of the formation fluid and analyzing the sample in a laboratory. However, as the formation fluid is brought from formation conditions (e.g., high temperature high pressure conditions), acid gases and salts may come out of solution, irreversibly changing the pH of the sample. Thus the analyzed sample may not be an accurate representation of the pH of the formation fluid at formation conditions.

Other methods of determining a pH of formation fluids include introducing a dye (e.g., phenol red, methylene blue, and/or cresol red) into the formation and correlating the pH of the formation fluid to the color of the dye. However, such dyes may not be formulated to determine the pH of the formation fluid with a desired level of accuracy. For example, some dyes may only be sensitive within a narrow pH range, such as a pH range of about 3.0 pH units. In addition, the dyes may be chemically unstable under formation conditions. Further, a continuous pH measurement may not be obtained unless the dye is continuously injected into the subterranean formation.

Other properties of the subterranean formation (e.g., salinity, wettability of formation surfaces, flow paths through the subterranean formation, etc.) may be determined using one or more tracer compounds. For example, water tracers may be introduced into the subterranean formation to estimate flow patterns between wells during enhanced oil recovery processes, such as, for example, water flooding. Some tracers may include a fluorophore (i.e., a compound that can re-emit light upon light excitation) and a presence of the tracer may be determined by fluorescence spectroscopy. However, the fluorophore may include organic molecules and rare-earth complexes that are toxic and/or radioactive and may contaminate the subterranean formation (e.g., aquifers located in the subterranean formation). Further, fluorophores may decompose at downhole conditions and may be subject to photobleaching (i.e., the photochemical alteration of the fluorophore such that it becomes permanently unable to fluoresce) and photo blinking (i.e., fluorescence intermittency).

BRIEF SUMMARY

Embodiments disclosed herein include systems and methods for determining at least one property of a subterranean formation. For example, in accordance with one embodiment, a system for determining at least one property of at least one fluid in at least one subterranean formation comprises a fluid delivery system configured and positioned to deliver a fluid into at least one of at least one subterranean formation and a wellbore extending through the at least one subterranean formation, a radiation source within the wellbore, the radiation source configured to generate excitation radiation, carbon quantum dots disposed in the fluid, and a detector within the wellbore, the detector configured to measure at least one fluorescence property of the carbon quantum dots.

In additional embodiments, a system for determining at least one property of at least one subterranean formation comprises at least one fiber optic cable within a wellbore extending through at least one subterranean formation, the at least one fiber optic cable including at least one optical fiber comprising carbon quantum dots, a radiation source coupled to the at least one optical fiber, the radiation source configured to generate excitation radiation for transmission through the at least one optical fiber, and a detector coupled to the at least one fiber optic cable, the detector configured to measure at least one fluorescence property of the carbon quantum dots.

In further embodiments, a method of forming carbon quantum dots comprises providing an electrolyte comprising a carbon source and a source of ions to an electrochemical cell, introducing the electrolyte between platinum electrodes of the electrochemical cell, and applying electrical current between the platinum electrodes to form carbon quantum dots including carbon from the carbon source.

In yet further embodiments, a method of determining at least one property within at least one subterranean formation comprises introducing at least one fiber optic cable into at least one of at least one subterranean formation and a wellbore extending into the at least one subterranean formation, transmitting excitation radiation through the at least one fiber optic cable from a radiation source coupled to the at least one fiber optic cable, exposing carbon quantum dots disposed in a fluid in the wellbore or on the at least one fiber optic cable to the excitation radiation, receiving, at an optical sensor coupled to the at least one fiber optic cable, an emitted radiation from the carbon quantum dots responsive to exposure of the carbon quantum dots to the excitation radiation, and measuring at least one of an emission spectrum and a fluorescence intensity of the emitted radiation at a detector coupled to the at least one fiber optic cable.

DETAILED DESCRIPTION

Figure 1:
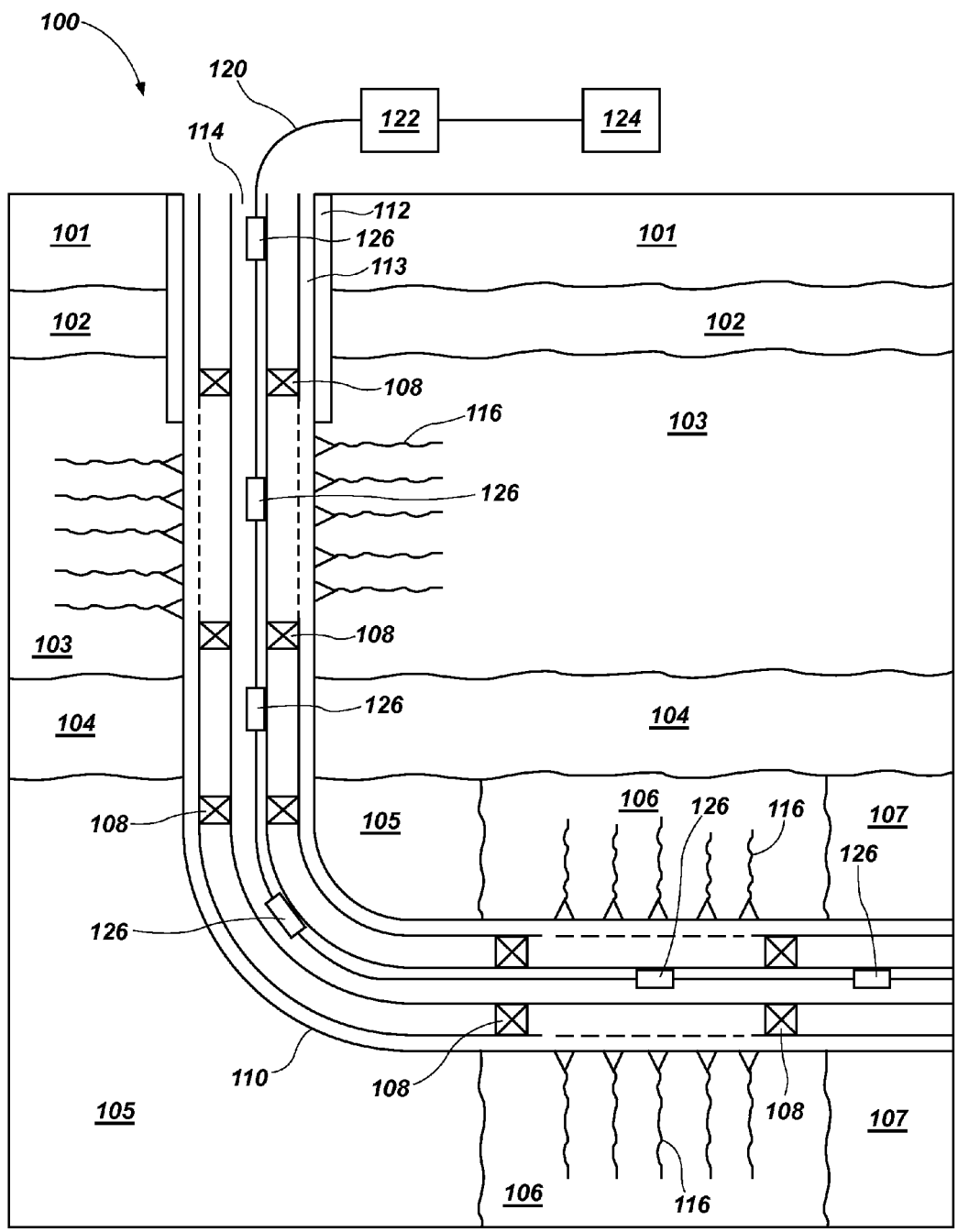
FIG. 1 is a simplified schematic illustrating a system including a wellbore within a subterranean formation, in accordance with embodiments of the disclosure.

The following description provides specific details, such as material types, compositions, and processing conditions in order to provide a thorough description of embodiments of the disclosure. However, a person of ordinary skill in the art will understand that the embodiments of the disclosure may be practiced without employing these specific details. Indeed, the embodiments of the disclosure may be practiced in conjunction with conventional techniques employed in the industry. In addition, the description provided below does not form a complete process flow for measuring properties within a subterranean formation or for forming carbon quantum dots. Only those process acts and structures necessary to understand the embodiments of the disclosure are described in detail below.

As used herein, the term "fluorescence property" means and includes any measurable property relating to the fluorescence of carbon quantum dots (CQDs). As non-limiting examples, fluorescence properties include a wavelength at which a material exhibits a peak absorption intensity, a wavelength at which a material exhibits a peak fluorescence intensity (e.g., a color of light emitted during fluorescence, such as when the fluorescence is in the visible spectrum), an excitation spectrum, an emission spectrum, an intensity of absorbed electromagnetic radiation, and an intensity of emitted electromagnetic radiation. The electromagnetic radiation may be anywhere within the electromagnetic spectrum, including, for example, the UV spectrum, the visible spectrum, and the infrared (IR) spectrum.

According to embodiments disclosed herein, a method of forming carbon quantum dots (CQDs) includes providing an electrochemical cell including an electrolyte comprising a carbon source, water, and at least another material. A current is applied across electrodes of the electrochemical cell to form carbon quantum dots comprising carbon from the carbon source. The carbon source may include at least one of (i.e., one or more of) nitrogen, boron, silicon, and phosphorus to form at least one of nitrogen-doped, boron-doped, silicon-doped, and phosphorus-doped carbon quantum dots, respectively. The carbon quantum dots may be water soluble, exhibit unique fluorescence properties depending on a size and chemical composition (e.g., doping) of the carbon quantum dots, may be stable at wide pH ranges and temperatures (e.g., up to about 400° C.), and may be resistant to photobleaching and photo blinking. Surfaces of the carbon quantum dots may be functionalized to form exposed hydrophilic surfaces, exposed hydrophobic surfaces, or exposed amphiphilic surfaces on the carbon quantum dots.

The fluorescence properties of the carbon quantum dots may be used to determine at least one property of at least one subterranean formation (e.g., a pH of the formation fluid, a wettability of formation surfaces, a production zone within the at least one subterranean formation, etc.). For example, the carbon quantum dots may exhibit a fluorescence property that is related to a pH to which the carbon quantum dots are exposed. Carbon quantum dots may be introduced into the subterranean formation and exposed to excitation radiation (e.g., an excitation wavelength). A radiation source (e.g., a light source) may be coupled to a fiber optic cable, which may transmit the excitation radiation to the carbon quantum dots. The carbon quantum dots may be disposed within at least one optical fiber of the fiber optic cable or may be coated onto at least a portion of the at least one optical fiber. Responsive to exposure to the excitation radiation, the carbon quantum dots may fluoresce (e.g., re-emit radiation at a different wavelength than the excitation wavelength). The emitted radiation may be transmitted through the at least one optical fiber to a detector that may be configured to measure at least one fluorescence property of the carbon quantum dots. In other embodiments, the carbon quantum dots are disposed in a fluid within the wellbore. A fluid delivery system may be configured to provide (e.g., deliver) the carbon quantum dots to the wellbore. The radiation source may be located within the wellbore and may be configured to provide the excitation radiation to the carbon quantum dots disposed within the fluid. The detector may be located within the wellbore and may be configured to measure at least one fluorescence property of the carbon quantum dots. The at least one fluorescence property may be correlated to at least one property (e.g., a pH) to which the carbon quantum dots are exposed.

The carbon quantum dots may be used as tracers to monitor fluid flow through the subterranean formation. For example, carbon quantum dots exhibiting different fluorescence properties may be introduced into different zones (e.g., producing zones, aquifer zones, etc.) of the subterranean formation. A produced fluid exhibiting a fluorescence property corresponding to a fluorescence property of carbon quantum dots introduced into a zone of the subterranean zone may be an indication that the produced fluid originated from the zone in which the carbon quantum dots were introduced. In other embodiments, a mixture of hydrophilic and hydrophobic carbon quantum dots exhibiting different fluorescence properties may be introduced into the subterranean formation. A ratio of hydrophilic carbon quantum dots to hydrophobic carbon quantum dots in a produced fluid may be determined by a fluorescence property of the produced fluid. The ratio may be employed as an indication of a wettability of surfaces of the subterranean formation (e.g., a ratio of water wet surfaces to oil wet surfaces in the subterranean formation).

FIG. 1 is a simplified schematic illustration of a wellbore system 100 extending through one or more subterranean formations. The subterranean formations may include a plurality of zones, including a first zone 101 proximate a surface of the earth, an aquifer zone 102 below the first zone 101, a second zone 103 below the aquifer zone 102, a third zone 104 below the second zone 103, a fourth zone 105 below the third zone 104, and a fifth zone 106 horizontally adjacent to the fourth zone 105. The subterranean formation may include one or more additional zones, such as a sixth zone 107 horizontally adjacent to the fifth zone 106. At least some of the zones may be hydrocarbon-bearing zones. For example, the second zone 103 and the fifth zone 106 may be hydrocarbon-bearing zones and may include fractures 116 through which hydrocarbons to be produced may travel during production. The other zones (e.g., the third zone 104, the fourth zone 105, and the sixth zone 107) may also contain hydrocarbons. Each of the zones may be isolated from other zones by at least one packer 108.

A wellbore 110 may extend through each of the different zones of the subterranean formation. Cement 112 may line the wellbore 110 at least through the first zone 101, the aquifer zone 102, and at least a portion of the second zone 103. A liner string 113 may line at least a portion of the wellbore 110. A production string 114 may extend through the subterranean formation and to a portion of the formation bearing hydrocarbons to be produced.

During formation and operation of the wellbore 110 (e.g., during drilling, completion, stimulation, production, etc.), it may be desirable to measure or estimate properties of fluids (e.g., drilling fluids, stimulation fluids, completion fluids, formation fluids, etc.) located within the wellbore 110, and properties of the subterranean formation through which the wellbore 110 extends. For example, it may be desirable to measure the pH of the formation fluid at formation conditions in real time.

As will be described in more detail below, at least one fluorescence property, such as at least one of (i.e., one or more of) an absorption spectrum, an absorption intensity, a peak absorption wavelength, an emission spectrum, a peak emission wavelength, and a fluorescence intensity of carbon quantum dots, may be related to a pH of a fluid surrounding the carbon quantum dots. The carbon quantum dots may be formulated to exhibit unique absorption and fluorescence properties associated with the size and the molecular composition of the carbon quantum dots. For example, the carbon quantum dots may be formulated to fluoresce at wavelengths corresponding to a color of the visible spectrum (e.g., violet, blue, cyan, green, yellow, orange, and red). The color of fluorescence may depend, at least in part, upon at least one of a size and a chemical composition of the carbon quantum dots. In some embodiments, the carbon quantum dots may be formulated to exhibit upconversion properties. For example, in some embodiments, the carbon quantum dots may be formulated to emit radiation at a shorter wavelength (and a corresponding higher energy) than radiation absorbed by the carbon quantum dots.

Accordingly, carbon quantum dots may be introduced into the subterranean formation at a zone where it is desired to determine the pH of a fluid within the wellbore (e.g., formation fluid). In some embodiments, the carbon quantum dots comprise a part of at least one optical fiber (e.g., the carbon quantum dots may comprise a coating on an optical fiber or the carbon quantum dots may be disposed within the optical fiber). The optical fiber including the carbon quantum dots may be exposed to fluid in communication with the subterranean formation. In other embodiments, the carbon quantum dots are introduced into the subterranean formation with a fluid delivery system configured to deliver a fluid having the carbon quantum dots suspended therein to the subterranean formation.

The pH of a fluid within the wellbore 110 may be determined by exposing the carbon quantum dots disposed within the wellbore 110 to an excitation radiation and measuring at least one of (i.e., one or more of) the absorption spectrum, the absorption intensity, the peak absorption wavelength (i.e., the peak of the absorption spectrum), the emission spectrum, the peak emission wavelength (i.e., the peak of the emission spectrum), and the fluorescence intensity of the carbon quantum dots responsive to exposure to the excitation radiation. The excitation radiation may be at a substantially monochromatic wavelength or may be at a plurality of wavelengths (i.e., polychromatic wavelengths).

With continued reference to FIG. 1, the wellbore system 100 may include a fiber optic cable 120 extending from a surface location of the subterranean formation to locations adjacent to one or more zones within the subterranean formation. The fiber optic cable 120 may extend along an interior of the production string 114, similar to a wireline, as is known to those of ordinary skill in the art, and may be run into the production string 114 as desired, or permanently deployed within the production string 114. Although the fiber optic cable 120 is illustrated as extending along an interior of the production string 114, the fiber optic cable 120 may be located at any suitable location within the wellbore system 100 relative to the production string 114. For example, the fiber optic cable 120 may be run along an exterior of the production string 114, or comprise part of a self-contained sensor package configured for wireless communication, as noted below.

The fiber optic cable 120 may be coupled to a radiation source 122 and to a detector 124. In some embodiments, the radiation source 122 and the detector 124 may be located at the surface above the subterranean formation, such as on or adjacent to the rig floor. As will be described herein, in other embodiments, one or more of the radiation source 122 and the detector 124 may be located within the wellbore 110. The radiation source 122 may be configured to emit electromagnetic radiation at one or more wavelengths (i.e., the excitation radiation) which may be transmitted through the fiber optic cable 120 to one or more locations within the subterranean formation. In some embodiments, the radiation source 122 comprises a laser configured to transmit the excitation radiation at a substantially monochromatic (e.g., a substantially fixed and uniform) wavelength. The substantially monochromatic wavelength may be any wavelength in the electromagnetic spectrum. In some embodiments, the substantially monochromatic wavelength may be within the ultraviolet spectrum, such as, for example, between about 100 nm and about 400 nm. In other embodiments, the radiation source 122 includes a broadband radiation source configured to provide the excitation radiation at more than one wavelength (e.g., polychromatic wavelengths). By way of non-limiting example, the radiation source 122 may include a light-emitting diode (LED) (e.g., a collimated LED, an uncollimated LED), a xenon lamp, a mercury lamp, or other suitable electromagnetic radiation source. In some embodiments, the excitation radiation is transmitted in pulses.

Figure 2A:
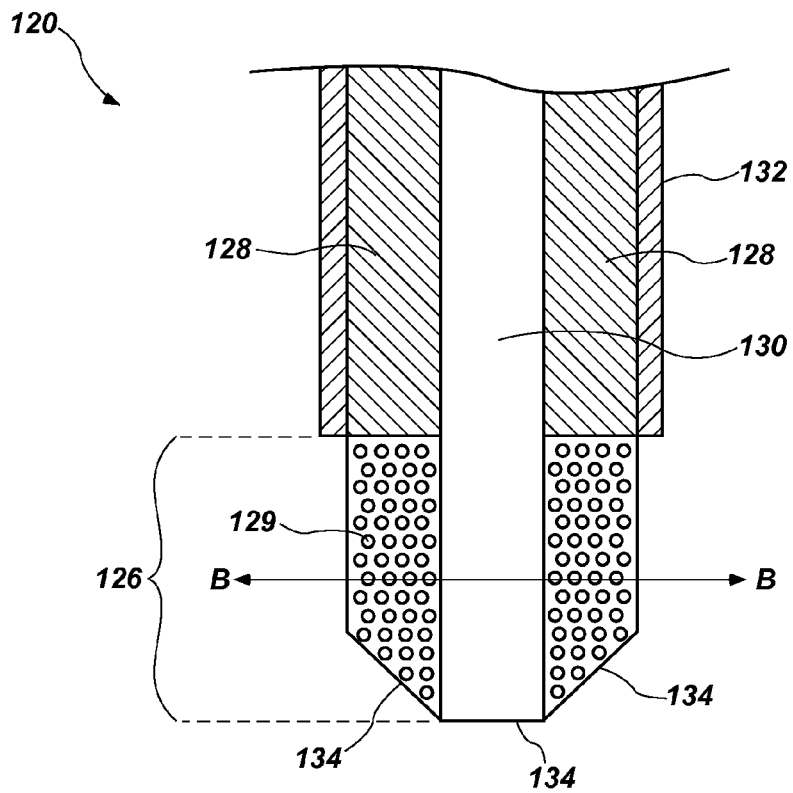
FIG. 2A is a simplified cross-sectional view illustrating a fiber optic cable, in accordance with embodiments of the disclosure.

The fiber optic cable 120 may include one or more optical sensors 126 configured to detect one or more fluorescence properties of the carbon quantum dots in the wellbore system 100. FIG. 2A is a simplified schematic representation of a fiber optic cable 120 including an optical sensor 126. The fiber optic cable 120 may include at least one optical fiber 128 within a sheath 132 configured to transmit the excitation radiation to the carbon quantum dots within the wellbore 110 and at least one optical fiber 130 within the sheath 132 configured to receive the radiation emitted from the carbon quantum dots. Each of the optical fibers 128 may be coupled to the radiation source 122 (FIG. 1) and each of the optical fibers 130 may be coupled to the detector 124 (FIG. 1). The optical sensor 126 may include at least one exposed portion of the optical fiber 128 and at least one exposed portion of the optical fiber 130.

Each of the optical fibers 128 may be configured to receive the excitation radiation independently of other optical fibers 128 and at differing wavelengths, intensities and, if applicable, pulse rates, radiation pulses from different optical fibers 128 being sent simultaneously or at offset time intervals. In other embodiments, each of the optical fibers 128 may be configured to receive excitation radiation of substantially the same wavelength, intensity and, if applicable, pulse rates and intervals as the other optical fibers 128. In yet other embodiments, the radiation source 122 may be configured to provide the excitation radiation at a substantially monochromatic wavelength and intensity to one of the optical fibers 128 and excitation radiation of another substantially monochromatic wavelength and intensity to another of the optical fibers 128.

A distal end of the optical fiber 128 may include what is known in the art as a "mirror finished" or a "polished" end 134. The mirror finished ends 134 of the optical fibers 128 may be angled with respect to a longitudinal axis of the optical fiber 128 and may be configured to reduce undesired reflection and/or scattering of the excitation radiation. For example, the mirror finished end 134 may be configured to reduce attenuation of the excitation radiation to be received through the optical fibers 130. The mirror finished ends 134 may be configured to substantially reflect light emitted by the carbon quantum dots to the detector 124.

Figure 2B:
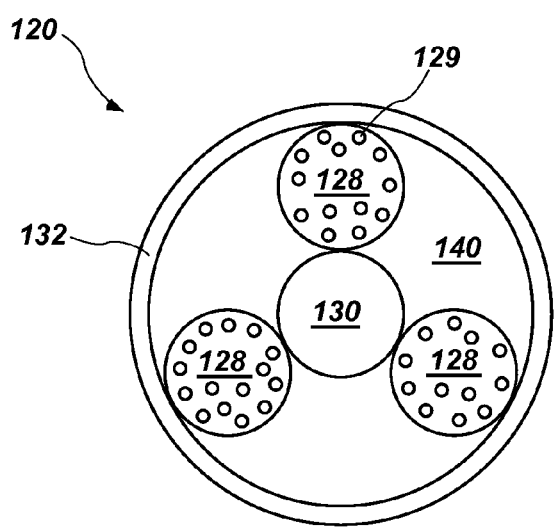
FIG. 2B is a simplified cross-sectional view of the fiber optic cable taken along section line B-B of FIG. 2A.

At least a portion of at least one optical fiber 128 may include carbon quantum dots 129 disposed therein. The carbon quantum dots 129 may be disposed within one or more optical fibers. FIG. 2B is a simplified cross-sectional view of the fiber optic cable 120 of FIG. 2A. The carbon quantum dots 129 may be disposed within and integral with the optical fibers 128. By way of non-limiting example, carbon quantum dots 129 may be dispersed in a composition (e.g., mixed in a molten solution) from which the optical fibers 128 are formed (e.g., extruded, drawn, cast, etc.). It is contemplated that, in some embodiments, the optical fibers 128 may include materials formulated to enhance optical properties of the optical fibers 128, such as, for example, titanium dioxide.

Portions of the optical fibers 128 may be exposed to a wellbore fluid 140 (e.g., drilling fluids, stimulation fluids, completion fluids, formation fluids, etc.). For example, at least a distal end of the optical fibers 128 may be exposed to the wellbore fluid 140. The portions of the optical fibers 128 that are exposed to the wellbore fluid 140 may include the carbon quantum dots 129 disposed therein. The excitation radiation from the radiation source 122 may be transmitted to the carbon quantum dots 129 of the optical fibers 128. Responsive to exposure to the excitation radiation, the carbon quantum dots 129 may emit radiation exhibiting at least one fluorescence property related to the pH of the formation fluid 140 surrounding the exposed portions of the optical fibers 128. The optical fiber 130 may receive the radiation emitted by the carbon quantum dots 129 and transmit the emitted radiation to the detector 124.

Figure 2C:
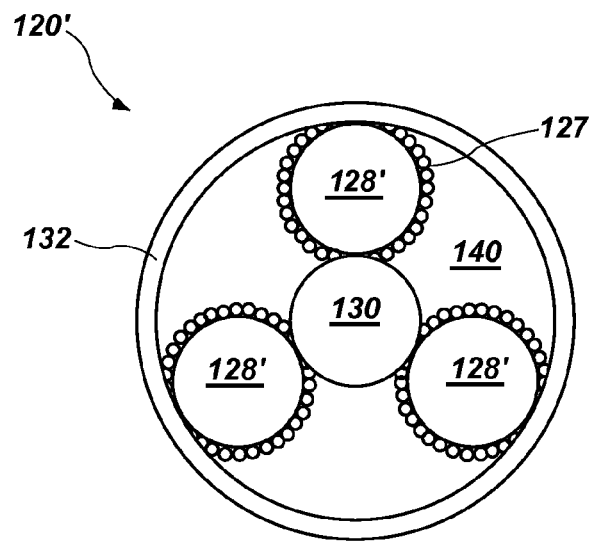
FIG. 2C is a simplified cross-sectional view of another fiber optic cable, in accordance with embodiments of the disclosure.

In other embodiments, the carbon quantum dots 129 may be disposed on at least one surface of at least one optical fiber. For example, a surface of at least one optical fiber may have a coating of the carbon quantum dots. FIG. 2C is a simplified cross-sectional view of a fiber optic cable 120' substantially similar to the fiber optic cable 120 of FIG. 2B, except that the fiber optic cable 120' includes optical fibers 128' having a coating 127 of carbon quantum dots thereon. In some embodiments, the coating 127 comprises a monolayer of carbon quantum dots. The coating 127 may substantially surround each of the optical fibers 128'. The coating 127 may be a substantially continuous layer around an entire circumference of each of the optical fibers 128'. The coating 127 may be in contact with the wellbore fluid 140, which may affect at least one fluorescence property of the carbon quantum dots of the coating 127.

The coating 127 may be located at, for example, the distal end of the optical fiber 128'. The excitation radiation from the radiation source 122 may be transmitted to the carbon quantum dots on the coating 127. Responsive to exposure to the excitation radiation, the carbon quantum dots may emit radiation exhibiting at least one fluorescence property related to the pH of the wellbore fluid 140 surrounding the coating 127.

The optical fibers 130 may be configured to receive the radiation emitted by the carbon quantum dots (e.g., radiation emitted from the coating 127) and transmit the emitted radiation to the detector 124, which may be located at a surface location. Each of the optical fibers 130 may be coupled to the detector 124.

Accordingly, in some embodiments, the carbon quantum dots may be introduced into the subterranean formation with the fiber optic cable 120, 120'. Radiation emitted by the carbon quantum dots on or within the optical fibers 128, 128' may be received by the optical fiber 130 and transmitted to the detector 124. Thus, the carbon quantum dots may be configured to continuously measure the pH of the fluid in the wellbore 110 without continuously introducing new carbon quantum dots into the subterranean formation.

Figure 2D:
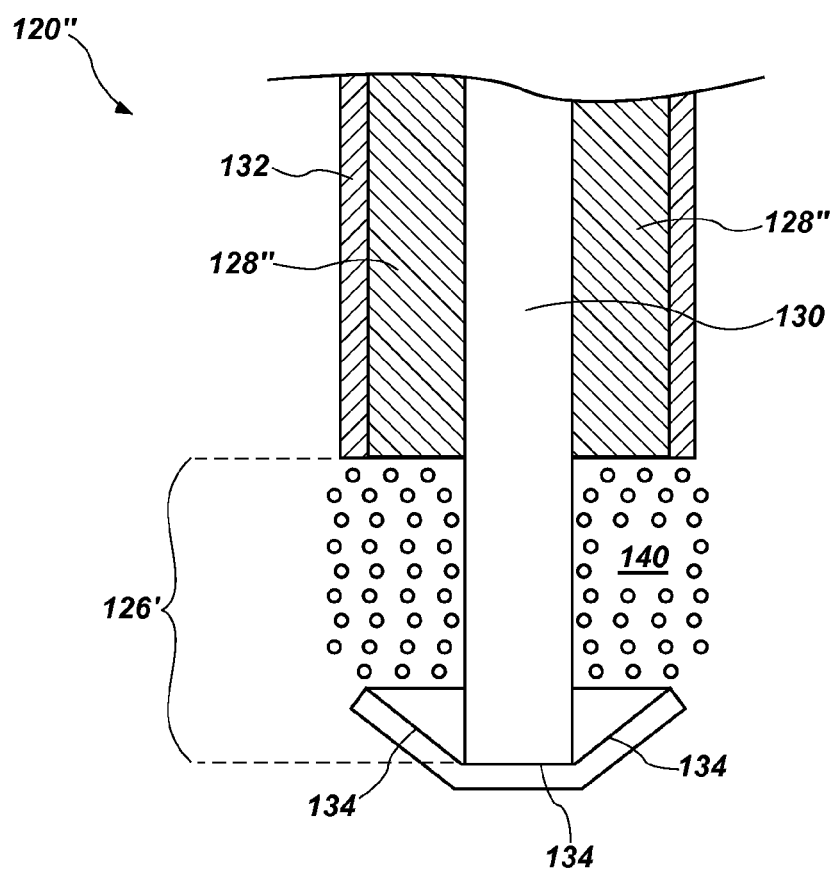
FIG. 2D is a simplified cross-sectional view illustrating a fiber optic cable, in accordance with other embodiments of the disclosure.

In other embodiments, the carbon quantum dots may not be coated on the optical fibers 128, 128', but may be disposed in the wellbore fluid 140. FIG. 2D illustrates an embodiment of another fiber optic cable 120" according to another embodiment of the disclosure. The fiber optic cable 120" may include an optical sensor 126' comprising optical fibers 128" configured to transmit excitation radiation to carbon quantum dots disposed within the wellbore 110 and at least one optical fiber 130 within the sheath 132 configured to receive the radiation emitted from the carbon quantum dots. The carbon quantum dots may be disposed in the wellbore fluid 140 proximate the optical fibers 128", 130. The concentration of the carbon quantum dots in the wellbore fluid 140 may be between about 50 parts per trillion (ppt) and about 10,000 parts per million (ppm), such as between about 50 ppt and about 500 ppt, between about 500 ppt and about 5,000 ppt (5 ppm), between about 5 ppm and about 500 ppm, or between about 500 ppm and about 10,000 ppm.

Excitation radiation may be transmitted through the optical fibers 128" to the carbon quantum dots in the wellbore fluid 140. Responsive to exposure to the excitation radiation, the carbon quantum dots may emit radiation that may be received by the optical fibers 130. The optical fiber 130 may transmit the emitted radiation to the detector 124. Thus, a pH of the fluid 140 proximate the optical fibers 128", 130 may be determined by disposing the carbon quantum dots in the wellbore fluid 140 and detecting at least one fluorescence property of the carbon quantum dots.

Accordingly, with reference again to FIG. 1, the radiation source 122 may be configured to pulse the excitation radiation to the carbon quantum dots within the wellbore 110. Carbon quantum dots proximate one or more of the optical sensors 126 may absorb the excitation radiation. Responsive to absorbing the excitation radiation, the carbon quantum dots may fluoresce at an emission wavelength (e.g., that may correspond to, for example, red light, yellow light, blue light, etc.). During fluorescence, the carbon quantum dots may re-emit radiation at a wavelength (i.e., an emission wavelength) that is different from the wavelength of the excitation radiation (i.e., the excitation wavelength).

The detector 124 may be configured to continuously measure at least one fluorescence property (e.g., one or more of the absorption spectrum, the peak absorption wavelength, the absorption intensity, the emission spectrum, the peak emission wavelength, and the fluorescence intensity) of the carbon quantum dots. The measured fluorescence property may be correlated to a pH of the formation fluid. Accordingly, the pH of the formation fluid may be measured in situ and in real time. The detector 124 may include or be coupled to a processor configured to estimate the pH of the formation fluid based on one or more of the absorption spectrum, the peak absorption wavelength, the absorption intensity, the emission spectrum, the peak emission wavelength, and the fluorescence intensity of the carbon quantum dots. In some embodiments, the detector is a spectrometer, such as a fluorescence spectrometer.

Although FIG. 2A through FIG. 2D illustrate optical fibers 128, 128', 128" configured to transmit the excitation radiation to the carbon quantum dots and optical fibers 130 configured to transmit the emitted radiation to the detector 124, it is contemplated that in some embodiments, the fiber optic cable 120 may include a single optical fiber. Excitation radiation may be transmitted through the optical fiber in pulses, such as every millisecond, every 10 milliseconds, or every 100 milliseconds. The fluorescence emitted by the carbon quantum dots may be transmitted back through the single optical fiber between excitation pulses and received by the detector 124. In other words, the excitation pulses may be separated in time such that the carbon quantum dots may fluoresce and the emitted fluorescent radiation may be measured at the detector 124 in between consecutive pulses of excitation radiation. Although FIG. 1 illustrates only one fiber optic cable 120 extending into the wellbore 110, the wellbore system 100 may include a plurality of fiber optic cables 120 extending into the wellbore 110. For example, in some embodiments, at least one fiber optic cable 120 may be configured to transmit the excitation radiation to the carbon quantum dots and at least one fiber optic cable 120 may be configured to receive and transmit the emitted radiation from the carbon quantum dots to the detector 124.

Figure 2E:
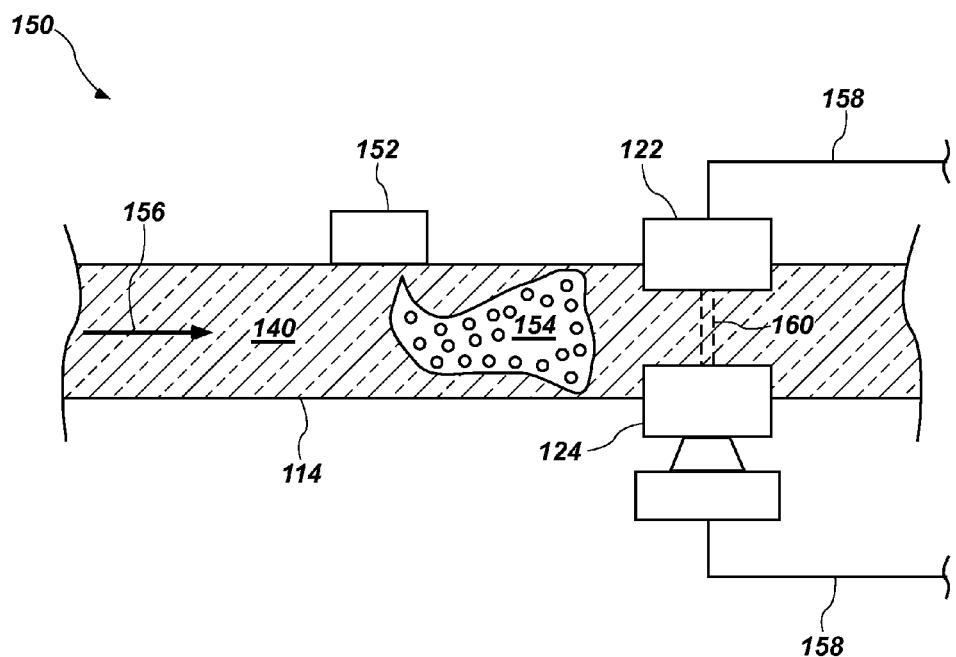
FIG. 2E is a simplified schematic illustrating a measuring system including a fluid delivery system, in accordance with yet other embodiments of the disclosure.

Although the radiation source 122 and the detector 124 are illustrated as being located at a surface location of the subterranean formation, at least one of the radiation source 122 and the detector 124 may be located within the wellbore 110. FIG. 2E is a simplified schematic illustrating a measuring system 150 according to another embodiment of the disclosure. The measuring system 150 includes a fluid deliver system 152 configured and positioned to deliver a carbon quantum dot-containing fluid 154 into the wellbore 110, such as into the production string 114. The radiation source 122 and the detector 124 may be located at a location downstream of the fluid deliver system 152. The wellbore fluid 140 may flow in the production string 114 in the direction indicated by arrow 156. The wellbore fluid 140 may carry the carbon quantum dot-containing fluid 154 to a location proximate the radiation source 122 and the detector 124. In some embodiments, the fluid delivery system 152 is located proximate the radiation source 122 and the detector 124, such as, for example, within about one meter of the radiation source 122 and the detector 124. The carbon quantum dot-containing fluid 154 may substantially mix with the wellbore fluid 140 prior to being exposed to excitation radiation 160 from the radiation source 122.

As the carbon quantum dots in the carbon quantum dot-containing fluid 154 are exposed to the excitation radiation 160 from the radiation source 122, the carbon quantum dots may fluoresce. Responsive to exposure to the excitation radiation 160, the carbon quantum dots may emit radiation that may be received by the detector 124, which, in some embodiments, may be located directly across from the radiation source 122. In other embodiments, the detector 124 may be located adjacent the radiation source 122, such that the carbon quantum dots pass the detector 124 directly after exposure to the excitation radiation 160. Accordingly, a pH of the wellbore fluid 140 may be determined by disposing the carbon quantum dots into the wellbore fluid 140 (e.g., via the carbon-quantum dot-containing fluid 154) and detecting at least one fluorescence property of the carbon quantum dots.

The detector 124 may be configured to transmit information about the detected fluorescence properties to the surface, such as by, for example, a wire 158 coupled to the detector 124 and configured to transmit the data to the surface, wireless communications, mud pulse telemetry, or other method suitable to transmit the data from the detector 124 located within the wellbore 110 to the surface of the subterranean formation.

Figure 3A:
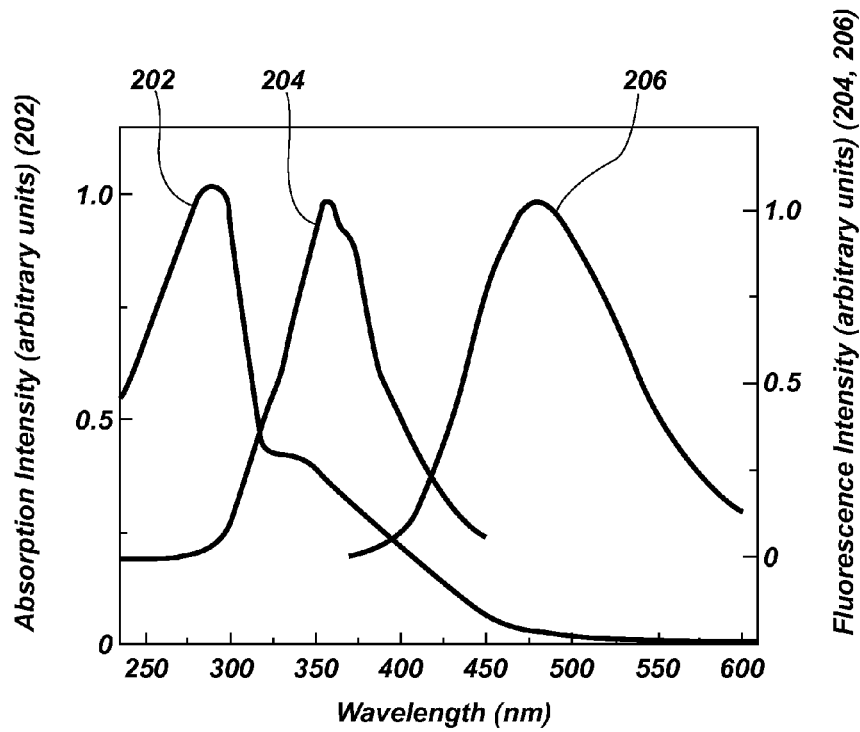
FIG. 3A is a graph illustrating an absorption spectrum, an excitation spectrum, and an emission spectrum of carbon quantum dots, in accordance with embodiments of the disclosure.

FIG. 3A illustrates an example of an absorption spectrum 202, an excitation spectrum 204, and an emission spectrum 206 of fluorescence of carbon quantum dots in a solution. The absorption spectrum 202 (y-axis of the absorption spectrum 202 illustrated on the left side of FIG. 3A) graphs the absorption intensity of the carbon quantum dots as a function of an excitation wavelength to which the carbon quantum dots are exposed. The peak absorption intensity occurs at a wavelength of approximately 275 nm. The excitation spectrum 204 (y-axis of the excitation spectrum 204 illustrated on the right side of FIG. 3A) graphs a radiation intensity of the excitation radiation as a function of the wavelength. The peak excitation intensity occurs at an excitation wavelength of approximately 355 nm. Although the excitation spectrum 204 is illustrated as shifted from the absorption spectrum 202, in some embodiments, the excitation spectrum 204 may be more closely aligned with the absorption spectrum 202. The emission spectrum 206 (y-axis of the emission spectrum 206 illustrated on the right side of FIG. 3B) graphs an intensity of the emitted fluorescence radiation emitted by the carbon quantum dots as a function of wavelength. The emission spectrum 206 illustrates that the peak fluorescence intensity occurs at an emission wavelength of approximately 480 nm (i.e., an emission of blue-colored light). The intensity of the peak emission wavelength of the emission spectrum 206 may increase or decrease, depending upon the pH of the solution in which the carbon quantum dots are disposed. Thus, the carbon quantum dots are exposed to excitation radiation at a substantially monochromatic wavelength and the wavelength of the peak emitted radiation (i.e., the wavelength of the peak fluorescence intensity) is shifted from the peak wavelength of the excitation radiation.

As described above, the absorption spectrum and the emission spectrum emitted by the carbon quantum dots may depend on a pH of the solution in which the carbon quantum dots are disposed. Thus, for the same excitation wavelength, a change in the pH of the formation fluid in which the carbon quantum dots are disposed may correspond to a change in one or more of the absorption spectrum, the corresponding peak absorption wavelength of excitation radiation absorbed by the carbon quantum dot, the emission spectrum, and the corresponding peak emission wavelength emitted by the carbon quantum dots.

Figure 3B:
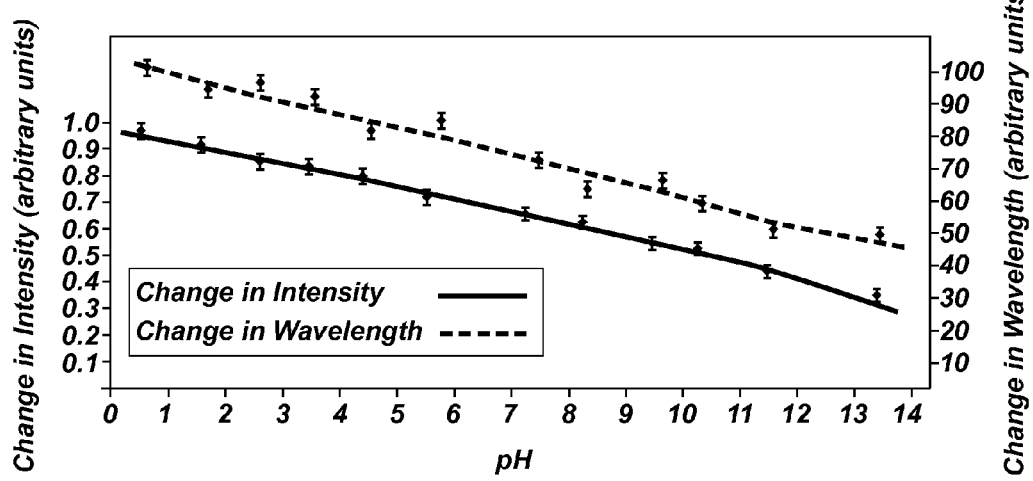
FIG. 3B is a graph illustrating a change in intensity and a change in wavelength as a function of pH for carbon quantum dots exposed to an excitation radiation having a substantially monochromatic wavelength, in accordance with embodiments of the disclosure.

FIG. 3B illustrates a change in intensity (e.g., one or more of an absorption intensity and an emission intensity) and a change in wavelength (e.g., a change in one or more of an excitation wavelength and an emission wavelength) as a function of pH for carbon quantum dots exposed to an excitation radiation at a substantially monochromatic wavelength. As illustrated in FIG. 3B, at a substantially monochromatic wavelength, the intensity of the carbon quantum dots (e.g., at the wavelength at which the carbon quantum dots exhibit the most fluorescence) may depend upon a pH of the solution in which the carbon quantum dots are disposed. Similarly, a wavelength at which carbon quantum dots absorb excitation radiation and an emission wavelength of the carbon quantum dots may change based on the pH to which the carbon quantum dots are exposed. Accordingly, in some embodiments, for a substantially monochromatic excitation wavelength, a pH of a formation fluid may be estimated based at least in part on one or more fluorescence or absorption properties of the carbon quantum dots, such as, for example, the absorption intensity (e.g., a change in the absorption intensity), the fluorescence intensity (e.g., a change in the fluorescence intensity), a change in the absorption wavelength (e.g., a change in the wavelength at which a highest intensity of excitation radiation is absorbed), a change in the emission radiation wavelength (e.g., a change in the wavelength at which a highest fluorescence intensity occurs), and combinations thereof. For example, at a substantially monochromatic wavelength, the emission radiation wavelength of the carbon quantum dots may shift depending on the pH of the solution in which the carbon quantum dots are disposed.

Hydrocarbons within the subterranean formation may include materials that fluoresce responsive to exposure to the excitation radiation. Fluorescence of such materials may undesirably increase noise in at least one of the fluorescence properties measured by the detector 124. However, such materials may have a shorter fluorescence lifetime than a fluorescence lifetime of the carbon quantum dots. In some embodiments, the detector 124 may be configured to measure the at least one fluorescence property of the carbon quantum dots after a time delay, such as in time-resolved fluorometric detection. Measuring the fluorescence of the carbon quantum dots after a time delay may reduce background noise caused by fluorescence of the materials in the hydrocarbons and increase the signal-to-noise ratio of the detector 124. The time delay may be between about 1 picosecond (ps) and about 100 microseconds (μs), such as between about 1 picosecond and about 1 nanosecond, between about 1 nanosecond and about 100 nanoseconds, between about 100 nanoseconds and about 1 microsecond, between about 1 microsecond and about 10 microseconds, or between about 10 microseconds and about 100 microseconds.

Accordingly, a fluid introduced into the subterranean formation may include the carbon quantum dots, or the carbon quantum dots may comprise at least a portion of a fiber optic cable 120, 120', such as within the at least one optical fiber 128 or as a coating on the at least one optical fiber 128'. The carbon quantum dots may be exposed to the excitation radiation. As described above, responsive to exposure to the excitation radiation, the carbon quantum dots may exhibit a fluorescence property that is, at least partially, dependent upon the pH of the fluid surrounding the carbon quantum dots. The emitted radiation may be transmitted from the carbon quantum dots to the detector 124, where at least one fluorescence property of the carbon quantum dots may be measured. The pH of fluid in which the carbon quantum dots are disposed may be determined based on a fluorescence property of the carbon quantum dots. The carbon quantum dots, either within the wellbore fluid 140 or within the at least one optical fiber 128, 128', may be substantially chemically inert (e.g., may not be subject to photobleaching) and may remain within the fluid or within the at least one optical fiber 128, 128' when exposed to formation conditions.

In addition to determining a pH of the formation fluid, it may be desirable to determine a location (e.g., a zone) from which produced fluids (e.g., hydrocarbons, water, etc.) originate. Carbon quantum dots exhibiting different fluorescence properties may be introduced into different zones of the subterranean formation. The carbon quantum dots in each of the different zones may be formulated to exhibit a different fluorescence property than carbon quantum dots introduced into the other zones. For example, carbon quantum dots having a first size may be introduced into a first zone and carbon quantum dots having a second size may be introduced into a second zone. In other embodiments, carbon quantum dots having a first chemical composition (e.g., undoped, nitrogen-doped, boron-doped, silicon-doped, phosphorus-doped, and combinations thereof) may be introduced into a first zone and carbon quantum dots having a different composition may be introduced into a second zone. Detection of a fluorescence property in a produced fluid corresponding to a fluorescence property of carbon quantum dots disposed in a zone of the subterranean formation may be an indication that the produced fluid originated from the corresponding zone. Detection of fluorescence properties in the produced fluid that correspond to carbon quantum dots introduced into different zones may be an indication that the produced fluid comprises formation fluid originating from each of the corresponding zones. A proportion of formation fluid originating from each zone may be determined by, for example, the relative value or intensity of the corresponding measured fluorescence property in the formation fluid.

As one non-limiting example, a first group of carbon quantum dots exhibiting a first fluorescence property may be introduced into at least one of the first zone 101, the aquifer zone 102, the second zone 103, the third zone 104, the fourth zone 105, the fifth zone 106, and the sixth zone 107 and at least a second group of carbon quantum dots exhibiting a second fluorescence property may be introduced into another of the first zone 101, the aquifer zone 102, the second zone 103, the third zone 104, the fourth zone 105, the fifth zone 106, and the sixth zone 107. An absorption spectrum, an emission spectrum or other fluorescence property of produced fluids may be measured to determine if any of the first group of carbon quantum dots or the second group of carbon quantum dots are present in the produced fluid. For example, an emission spectrum of the produced fluid may be used to determine a proportion of the produced fluid that originated from each zone based on the fluorescence intensity of the carbon quantum dots introduced into each zone. As another example, carbon quantum dots may be introduced proximate the aquifer zone 102. Produced fluids may be analyzed to determine if the produced fluids include a fluorescence property of the carbon quantum dots introduced into the aquifer zone 102. Identification of the corresponding fluorescence property may be an indication that the produced fluid includes water from the aquifer zone 102. In some embodiments, the first group of carbon quantum dots may include undoped carbon quantum dots and the at least a second group of carbon quantum dots may be doped with one or more of nitrogen, boron, silicon, and phosphorus. In other embodiments, the first group of carbon quantum dots may be undoped or may be doped with nitrogen, boron, silicon, or phosphorus and the at least a second group of carbon quantum dots may be another of undoped or doped with nitrogen, boron, silicon, or phosphorus.

In some embodiments, the carbon quantum dots may be introduced into the subterranean formation during stimulation processes. Stimulation processes such as, for example, hydraulic fracturing (i.e., "fracking") may be used to enhance hydrocarbon recovery from a hydrocarbon-bearing subterranean formation. In hydraulic fracturing operations, hydraulic fractures may be formed by injecting a fluid (e.g., water) containing additives and including a suspended proppant material (e.g., sand, ceramics, etc.) into a targeted subterranean formation under elevated pressure conditions sufficient to cause the hydrocarbon-bearing formation material to fracture. The carbon quantum dots may be included in the fracturing fluid. Carbon quantum dots introduced into each zone of the subterranean formation may exhibit a different fluorescence property than carbon quantum dots introduced into other zones of the subterranean formation. By way of non-limiting example, carbon quantum dots introduced into a first zone with a first fracturing fluid may be formulated to fluoresce at wavelengths that correspond to blue light (e.g., at wavelengths of about 450 nm) and carbon quantum dots introduced into a second zone with a second fracturing fluid may be formulated to fluoresce at wavelengths that correspond to red light (e.g., at wavelengths of about 700 nm). An emission spectrum (e.g., a fluorescence color) of produced fluid may indicate whether the produced fluid originated from the first zone or the second zone.

In yet other embodiments, the carbon quantum dots may be used as a tracer to determine fluid flow paths through the subterranean formation. The carbon quantum dots may be introduced into an injection well with a stimulation fluid during at least one of water flooding, steam assisted gravity drainage, steam flooding, cyclic steam stimulation, or other enhanced oil recovery stimulation processes. Fluids produced at one or more wells proximate the injection well may be analyzed for the presence of the carbon quantum dots in the produced fluid. The presence of carbon quantum dots in at least one well proximate the injection well may indicate that the stimulation fluid has traveled from the injection well to the well where the carbon quantum dots are detected. A first well producing a fluid with more carbon quantum dots than a produced fluid at a second well may be an indication that a greater amount of the stimulation fluid flowed from the injection well to the first well than from the injection well to the second well.

The carbon quantum dots may be formulated to interact with surfaces of the subterranean formation. For example, exposed surfaces of the carbon quantum dots may be functionalized with at least one functional group, such as with at least one hydrophilic group, at least one hydrophobic (e.g., oleophilic) group, and combinations thereof (e.g., to form amphiphilic surfaces). Hydrophilic groups on surfaces of the carbon quantum dots may interact with water wet surfaces of the subterranean formation and hydrophobic groups may interact with oil wet surfaces of the subterranean formation.

In some embodiments, the hydrophilic carbon quantum dots may be formulated to exhibit a different fluorescence property than the hydrophilic carbon quantum dots. For example, the hydrophilic carbon quantum dots may have a different size than the hydrophobic carbon quantum dots. In other embodiments, the hydrophilic carbon quantum dots are doped with at least one of nitrogen, boron, silicon, phosphorus, etc., and the hydrophobic carbon quantum dots are undoped or doped with at least another of nitrogen, boron, silicon, and phosphorus.

A mixture of hydrophilic and hydrophobic carbon quantum dots may be introduced into the subterranean formation, such as during, for example, water flooding, steam assisted gravity drainage, steam flooding, cyclic steam stimulation, or other enhanced oil recovery stimulation processes. A produced fluid may include at least one of the hydrophilic carbon quantum dots and the hydrophobic carbon quantum dots. A ratio of formation surfaces that are water wet relative to formation surfaces that are oil wet may correspond to a proportion of hydrophilic carbon quantum dots to hydrophobic carbon quantum dots in the produced fluid. The proportion of hydrophilic carbon quantum dots to hydrophobic carbon quantum dots may be determined by, for example, comparing the fluorescence intensity at the peak emission wavelength of the hydrophilic carbon quantum dots to the fluorescence intensity at the peak emission wavelength of the hydrophobic carbon quantum dots. Information about the wettability of the formation surfaces may be particularly useful where stimulation methods include expensive fluids, such as those including surfactants, micellar fluids, or polymers. Where the formation includes more water wet surfaces than oil wet surfaces, an aqueous-based stimulation fluid may be used during further stimulation procedures. Where the formation includes more oil wet surfaces than water wet surfaces, a non-polar stimulation fluid may be used during further stimulation procedures.

It is contemplated that carbon quantum dots exhibiting different fluorescence properties may be introduced into various zones of the subterranean formation (e.g., such as on an optical fiber 128, 128', or introduced into the wellbore fluid 140 at different zones of the subterranean formation. In some embodiments, between about one and about twenty different types of carbon quantum dots, each exhibiting one or more different fluorescence properties than the other types of carbon quantum dots, may be introduced into one or more different zones of the subterranean formation.

Although the carbon quantum dots have been described as being dispersed within a wellbore, it is contemplated that the carbon quantum dots may be used to identify a source of a product in a product supply chain. By way of non-limiting example, the carbon quantum dots may be dispersed in a hydrocarbon supply to indicate a source of the hydrocarbons during distribution thereof. A fluorescence property of the carbon quantum dots in the hydrocarbons may be an indication of the source of the hydrocarbons.

Figure 4:
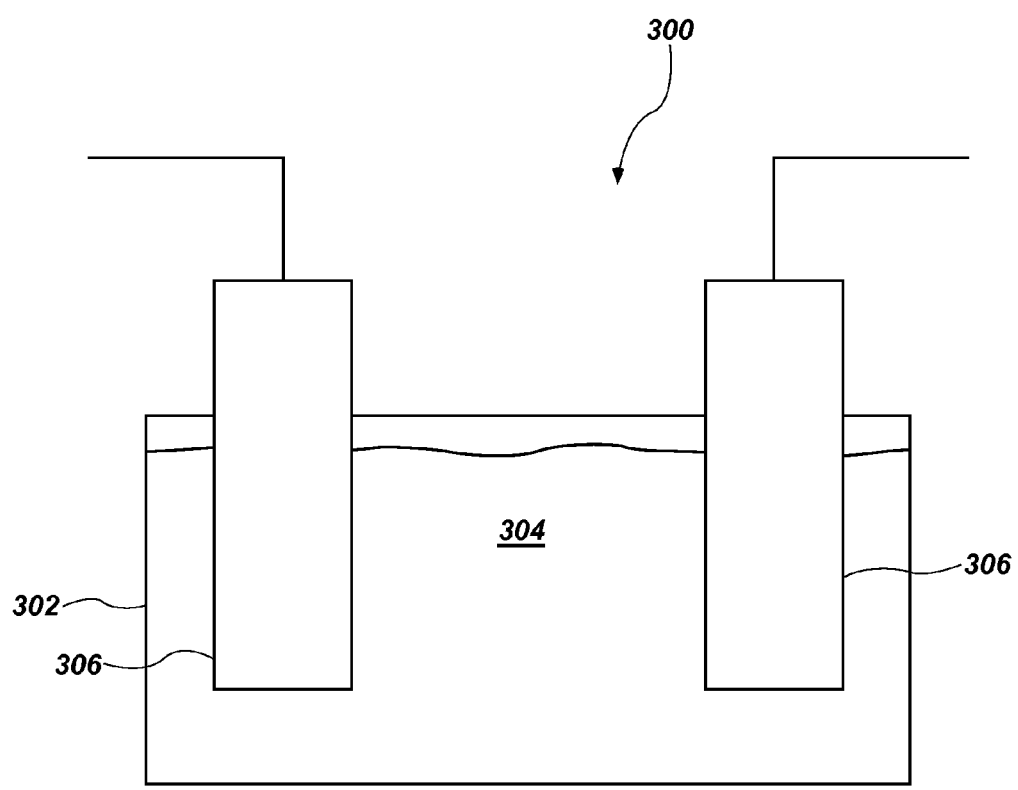
FIG. 4 is a simplified cross-sectional view of an electrochemical cell for forming carbon quantum dots, in accordance with embodiments of the disclosure.

FIG. 4 illustrates a simplified cross-sectional view of a configuration that may be used in a method of forming the carbon quantum dots described herein. The method includes providing an electrolyte 304 and electrodes 306 in a container 302 to form an electrochemical cell 300. Electrical current may be applied to the electrochemical cell 300 to form carbon quantum dots from a carbon source located in the electrolyte 304.

The container 302 may be any vessel or container suitable for holding the electrolyte 304 before, during, or after the electrochemical process of the disclosure, as described in further detail below. By way of non-limiting example, the container 302 may comprise a glass beaker configured to receive and hold the electrolyte 304 and the electrodes 306.

The electrolyte 304 may include at least one carbon source formulated for providing carbon for forming the carbon quantum dots during the electrochemical process. The electrolyte 304 may further include a source of ions, such as an acid, a base, or a buffer. In some embodiments, the source of ions includes a hydroxide, such as, for example, sodium hydroxide (NaOH), potassium hydroxide (KOH), cesium hydroxide (CsOH), magnesium hydroxide ($Mg(OH)_2$), calcium hydroxide ($Ca(OH)_2$), and barium hydroxide ($Ba(OH)_2$). In some embodiments, the at least another material has a concentration of about 1 molar and may be formulated such that the electrolyte 304 has a pH between about 13 and about 14.

The carbon source may constitute between about 1 volume percent and about 100 volume percent of the electrolyte 304, such as between about 1 volume percent and about 10 volume percent, between about 10 volume percent and about 25 volume percent, between about 25 volume percent and about 50 volume percent, and between about 50 volume percent and about 100 volume percent. The carbon source may be dispersed in water. In some embodiments, a ratio of the carbon source to water is approximately one to two (1:2).

The carbon source may include any water soluble carbon-containing material. In some embodiments, the carbon source is an alcohol, such as methanol, ethanol, propanol, butanol, combinations thereof, etc. In some embodiments, the carbon source is ethanol. Carbon quantum dots formed from such carbon sources may comprise carbon, hydrogen, and oxygen (e.g., may be undoped).

The carbon-quantum dots may be formulated to include at least one of nitrogen, boron, silicon, and phosphorus. The electrolyte 304 may be formulated to include at least one of a nitrogen source, a boron source, a silicon source, and a phosphorus source. The nitrogen source, the boron source, the silicon source, and the phosphorus source may also include carbon. Suitable nitrogen-containing carbon sources may include amino alcohols, such as, for example, ethanolamine ($C_2H_7NO$), diethanolamine ($C_4H_{11}NO_2$), and triethanolamine ($C_6H_{15}NO_3$). The nitrogen-containing carbon source may include a 2-aminoalcohol, such as, for example, 2-amino-1-propanol (alaninol) ($C_3H_9NO$), 2-amino-1,3-propanediol (serinol) ($C_3H_9NO_2$), tryptophanol ($C_{11}H_{14}N_2O$), a 1-amino-2-propanol ($C_3H_9NO$), and a propanolamine, such as metoprolol ($C_{15}H_{25}NO_3$), nadolol ($C_{17}H_{27}NO_4$), and phenylpropanolamine ($C_9H_{13}NO$), or any other water soluble carbon source including nitrogen.

Suitable boron-containing carbon sources may include water soluble organoboranes, such as, for example, a trialkylborane (($R_1R_2R_3B$), wherein $R_1$, $R_2$, and $R_3$ are alkyl groups. Suitable trialkylboranes may include, for example, trimethylborane (($CH_3)_3B$), triethylborane (($C_2H_5)_3B$), and tripropylborane (($C_3H_7)_3B$). Other boron-containing sources may include diborane ($H_6B_2$), a carborane, decaborane ($B_{10}H_{14}$), a boronic acid, such as, for example, phenylboronic acid ($C_6H_7BO_2$), methylboronic acid ($CH_3B(OH)_2$), and propenylboronic acid ($C_3H_5B(OH)_2$). Other boron-containing sources may include a boratebenzene (a borabenzene), such as, for example, 1-boratanaphthalene, 9-borataanthracene, boracyclooctantetraene, and 2,2'-diboratabiphenyl.

In some embodiments, the electrolyte 304 includes a compound including a nitrogen source and a boron source. For example, the electrolyte 304 may include a borane-amine complex, such as borane trimethylamine (($CH_3)_3NBH_3$) and borane tert-butylamine complex (($CH_3)_3CNH_2BH_3$).

Suitable silicon-containing carbon sources may include hydroxyalkylsilanes, (e.g., hydroxymethyltrimethylsilane ($HOCH_2Si(CH_3)_3$), hydroxyethoxysilatrane ($C_8H_{17}NO_5Si$)), and other water soluble organosilicon compounds.

Suitable phosphorus-containing compounds may include phosphate esters such as, for example, a phosphatidylcholine, triphenylphosphate ($OP(OC_6H_5)_3$), cyclophosphamide ($C_7H_{15}Cl_2N_2O_2P$), and parathion ($C_{10}H_{14}NO_5PS$), phosphonic acids and their esters, such as, for example, glyphosate ($C_3H_8NO_5P$), phosphoranes, such as, for example, pentaphenylphosphorane ($P(C_6H_5)_5$), and organophosphorus compounds, such as, for example, triphenylphosphine ($P(C_6H_5)_3$), phosphites, phosphonites, and phosphinites.

Accordingly, the carbon quantum dots may be doped with at least one of nitrogen, boron, silicon, and phosphorus. The fluorescence properties of the carbon quantum dots may depend on the composition of the electrolyte 304 (e.g., the carbon source) from which the carbon quantum dots are formed.

At least one of the nitrogen-containing carbon source, the boron-containing carbon source, the silicon-containing carbon source, and the phosphorus-containing carbon source may constitute between about 0 volume percent and about 100 volume percent of the carbon source, such as between about 1 volume percent and about 10 volume percent, between about 10 volume percent and about 25 volume percent, between about 25 volume percent and about 50 volume percent, or between about 50 volume percent and about 100 volume percent of the carbon source.

The electrodes 306 may include at least one anode and at least one cathode. In some embodiments, each of the electrodes 306 comprises platinum. The electrodes 306 may be coupled to a power supply configured to provide an electrical current to the electrochemical cell 300. A current may be applied to the electrochemical cell 300 for a sufficient period of time to form carbon quantum dots from the electrolyte 304. By way of non-limiting example, the applied current density may be within a range extending from about 100 milliamperes per square centimeter ($mA/cm^2$) to about 1,100 $mA/cm^2$ (e.g., from about 100 $mA/cm^2$ to about 500 $mA/cm^2$, from about 500 $mA/cm^2$ to about 1,000 $mA/cm^2$, or from about 1,000 $mA/cm^2$ to about 1,100 $mA/cm^2$). In some embodiments, the applied current density is approximately 1,100 $mA/cm^2$. A voltage may be applied between the electrodes 306 during the electrochemical reaction process. In some embodiments, a voltage of approximately 10 volts may be applied between the electrodes 306. Accordingly, the carbon quantum dots may be formed without using a carbon-containing electrode, such as a graphite electrode. Even when using an electrode that includes carbon, such as a graphite electrode, the carbon in the resulting carbon quantum dots may not include any significant amount of carbon that originated from the electrode.

Although FIG. 4 illustrates two electrodes 306, the electrochemical cell 300 may include any number of electrodes 306 (e.g., three, four, five, etc.).

After a suitable period of time, carbon quantum dots may form in the electrochemical cell 300. The electrolyte 304 may be evaporated and any solids may be collected. The solids may include amorphous carbon quantum dots. The carbon quantum dots may include C=C bonds and C—O functional groups. The carbon quantum dots may be undoped, nitrogen-doped, boron-doped, silicon-doped, phosphorus-doped, and combinations thereof. For example, at least some of the carbon quantum dots may include one of nitrogen, boron, silicon, and phosphorus and at least some of the carbon quantum dots may include at least another of nitrogen, boron, silicon, and phosphorus.

The carbon quantum dots may be generally spherical in shape having diameters ranging from between about 1 nm to about 10 nm. The carbon quantum dots may be separated into narrower size ranges by suitable methods, which may include dialysis. For example, the carbon quantum dots may be passed through at least one membrane having a pore size corresponding to a desired size of the carbon quantum dots. The separated carbon quantum dots may have a diameter ranging from between about 1 nm and about 3 nm, between about 3 nm and about 5 nm, or between about 5 nm and about 10 nm. Carbon quantum dots having different sizes may exhibit different fluorescence properties.

The carbon quantum dots may be soluble in aqueous-based solutions. After evaporation of the electrolyte 304, the carbon quantum dots may include exposed hydroxyl groups, exposed carboxyl groups, and combinations thereof. In some embodiments, exposed surfaces of the carbon quantum dots may be functionalized with at least one of additional hydrophilic functional groups or hydrophobic functional groups. Non-limiting examples of hydrophilic groups include, for example, a hydroxyl group, a carboxyl group, an amine group, a thiol group, and a phosphate group. Non-limiting examples of hydrophobic groups include, for example, an alkyl group, an alkenyl group, an alkynyl group, and an aryl group.

In some embodiments, a hydrophilic group or a hydrophobic group may be attached to the carbon quantum dots in a condensation reaction or a hydrolysis reaction, such as described in U.S. patent application Ser. No. 14/169,432, filed Jan. 31, 2014, and titled "NANO-SURFACTANTS FOR ENHANCED OIL RECOVERY, AND METHODS OF FORMING AND USING SUCH NANO-SURFACTANTS," or a reaction mechanism described in U.S. patent application Ser. No. 14/519,496, filed Oct. 21, 2014, and titled "SUSPENSIONS FOR ENHANCED HYDROCARBON RECOVERY, AND METHODS OF RECOVERING HYDROCARBONS USING THE SUSPENSIONS," the disclosure of each of which applications is hereby incorporated herein in its entirety by this reference. For example, a hydrophilic precursor or a hydrophobic precursor may include a hydrolyzable group and may be attached to a surface of the carbon quantum dots by hydrolyzing the hydrolyzable group. In other embodiments, a hydrophilic or hydrophobic group may be attached to the carbon quantum dots by a condensation reaction between the carbon quantum dots and one of a hydrophilic precursor and a hydrophobic precursor.

The carbon quantum dots may be stable at elevated temperatures (e.g., up to about 400° C.) and a wide range of pH (e.g., a pH between about 0 and about 14.0). Emission spectra of the carbon quantum dots may be dependent upon the size and composition of the carbon quantum dots. Accordingly, carbon quantum dots exhibiting different fluorescence properties (e.g., peak emission wavelengths) may be formed in the electrochemical cell 300.

Additional non-limiting example embodiments of the disclosure are set forth below.

Embodiment 1

A system for determining at least one property of at least one fluid in at least one subterranean formation, the system comprising: a fluid delivery system configured and positioned to deliver a fluid into at least one of at least one subterranean formation and a wellbore extending through the at least one subterranean formation; a radiation source within the wellbore, the radiation source configured to generate excitation radiation; carbon quantum dots disposed in the fluid; and a detector within the wellbore, the detector configured to measure at least one fluorescence property of the carbon quantum dots.

Embodiment 2

The system of Embodiment 1, wherein the carbon quantum dots comprise undoped carbon quantum dots.

Embodiment 3

The system of Embodiment 1, wherein the carbon quantum dots are doped with one or more of nitrogen, boron, silicon, and phosphorus.

Embodiment 4

The system of any one of Embodiments 1 through 3, wherein the carbon quantum dots comprise a first group of carbon quantum dots and at least a second group of carbon quantum dots, the first group of carbon quantum dots formulated to exhibit a different fluorescence property than the at least a second group of carbon quantum dots.

Embodiment 5

The system of Embodiment 4, wherein the first group of carbon quantum dots is dispersed in a first zone of the subterranean formation and the at least a second group of carbon dots is disposed in at least a second zone of the subterranean formation.

Embodiment 6

The system of any one of Embodiments 1 through 5, wherein the radiation source comprises a laser configured to generate excitation radiation of a substantially monochromatic wavelength or a broadband radiation source comprising one of a collimated LED, an uncollimated LED, or a white light.

Embodiment 7

The system of any one of Embodiments 1 through 6, wherein the carbon quantum dots include one or more of hydrophilic exposed surfaces and oleophilic exposed surfaces.

Embodiment 8

A system for determining at least one property of at least one subterranean formation, the system comprising: at least one fiber optic cable within a wellbore extending through at least one subterranean formation, the at least one fiber optic cable including at least one optical fiber comprising carbon quantum dots; a radiation source coupled to the at least one optical fiber, the radiation source configured to generate excitation radiation for transmission through the at least one optical fiber, and a detector coupled to the at least one fiber optic cable, the detector configured to measure at least one fluorescence property of the carbon quantum dots.

Embodiment 9

The system of Embodiment 8, wherein the carbon quantum dots are disposed within the at least one optical fiber.

Embodiment 10

The system of Embodiment 8, wherein the at least one optical fiber comprises a coating of the carbon quantum dots on at least a portion thereof.

Embodiment 11

The system of Embodiment 10, wherein the coating comprises a monolayer of the carbon quantum dots.

Embodiment 12

The system of any one of Embodiments 8 through 11, wherein the carbon quantum dots comprise a first group of undoped carbon quantum dots and at least a second group of carbon quantum dots doped with one or more of nitrogen, boron, silicon, and phosphorus.

Embodiment 13

The system of any one of Embodiments 8 through 12, further comprising at least another optical fiber coupled to the detector and configured to transmit emitted radiation from the carbon quantum dots to the detector.

Embodiment 14

The system of any one of Embodiments 8 through 11, or 13, wherein the carbon quantum dots comprise one or more of nitrogen, boron, silicon, and phosphorus.

Embodiment 15

The system of any one of Embodiments 8 through 14, wherein the detector is configured to measure at least one of an absorption spectrum, an emission spectrum, and a fluorescence intensity of the carbon quantum dots.

Embodiment 16

A method of forming carbon quantum dots, the method comprising: providing an electrolyte comprising a carbon source and a source of ions to an electrochemical cell; introducing the electrolyte between platinum electrodes of the electrochemical cell; and applying electrical current between the platinum electrodes to form carbon quantum dots including carbon from the carbon source.

Embodiment 17

The method of Embodiment 16, wherein providing an electrolyte comprising a carbon source comprises forming an electrolyte comprising one or more of ethanol and ethanolamine.

Embodiment 18

The method of Embodiment 16 or Embodiment 17, further comprising forming the electrolyte from one or more of a nitrogen source, a boron source, a silicon source, and a phosphorus source.

Embodiment 19

The method of any one of Embodiments 16 through 18, further comprising forming at least some carbon quantum dots comprising one of nitrogen, boron, silicon, and phosphorus and at least some carbon quantum dots comprising at least another of nitrogen, boron, silicon, and phosphorus.

Embodiment 20

The method of any one of Embodiment 16 through 19, further comprising forming hydrophilic surfaces on the carbon quantum dots or forming oleophilic surfaces on the carbon quantum dots.

Embodiment 21

A method of determining at least one property within at least one subterranean formation, the method comprising: introducing at least one fiber optic cable into at least one of at least one subterranean formation and a wellbore extending into the at least one subterranean formation; transmitting excitation radiation through the at least one fiber optic cable from a radiation source coupled to the at least one fiber optic cable; exposing carbon quantum dots disposed in a fluid in the wellbore or on the at least one fiber optic cable to the excitation radiation; receiving, at an optical sensor coupled to the at least one fiber optic cable, an emitted radiation from the carbon quantum dots responsive to exposure of the carbon quantum dots to the excitation radiation; and measuring at least one of an emission spectrum and a fluorescence intensity of the emitted radiation at a detector coupled to the at least one fiber optic cable.

Embodiment 22

The method of Embodiment 21, wherein measuring at least one of an emission spectrum and a fluorescence intensity of the emitted radiation at a detector comprises measuring the at least one of an emission spectrum and the fluorescence intensity after a time delay.

Embodiment 23

The method of Embodiment 21 or Embodiment 22, wherein introducing at least one fiber optic cable into at least one of at least one subterranean formation and a wellbore comprises introducing at least one fiber optic cable comprising at least one surface coated with carbon quantum dots into at least one of the at least one subterranean formation and the wellbore.

Embodiment 24

The method of any one of Embodiment 21 through 23, further comprising disposing a fluid comprising carbon quantum dots doped with one or more of nitrogen, boron, and phosphorus into at least one of the at least one subterranean formation and the wellbore.

Embodiment 25

The method of any one of Embodiment 21 through 23, further comprising introducing carbon quantum dots exhibiting a first fluorescence property into a first zone of the at least one subterranean formation and introducing carbon quantum dots having a second fluorescence property into a second zone of the at least one subterranean formation.

Although the foregoing description contains many specifics, these are not to be construed as limiting the scope of the disclosure, but merely as providing certain embodiments. Similarly, other embodiments may be devised that do not depart from the scope of the disclosure. For example, features described herein with reference to one embodiment also may be provided in others of the embodiments described herein. The scope of the invention is, therefore, indicated and limited only by the appended claims and their legal equivalents, rather than by the foregoing description. All additions, deletions, and modifications to embodiments of the disclosure, as described and illustrated herein, which fall within the meaning and scope of the claims, are encompassed by the disclosure.

What is claimed is:

1. A system for determining at least one property of at least one fluid in at least one subterranean formation, the system comprising:
   a fluid delivery system configured and positioned to deliver a fluid into at least one of at least one subterranean formation and a wellbore extending through the at least one subterranean formation;
   a radiation source within the wellbore, the radiation source configured to generate excitation radiation;
   carbon quantum dots comprising a carbon core, the carbon core exhibiting at least one fluorescence property disposed in the fluid, wherein the carbon quantum dots comprise at least:
      a first group of carbon quantum dots exhibiting a first fluorescence property responsive to exposure to electromagnetic radiation from the radiation source; and
      a second group of carbon quantum dots formulated to exhibit a different fluorescence property than the first fluorescence property exhibited by the first group of carbon quantum dots responsive to exposure to the electromagnetic radiation from the radiation source; and
   a detector within the wellbore, the detector configured to measure the at least one fluorescence property of the carbon core of the first group of carbon quantum dots and the second group of carbon quantum dots.

2. The system of claim 1, wherein at least one of the first group of carbon quantum dots and the second group of carbon quantum dots comprise undoped carbon quantum dots.

3. The system of claim 1, wherein the first group of carbon quantum dots are doped with one or more of nitrogen, boron, silicon, or phosphorus and the second group of carbon quantum dots are doped with another of nitrogen, boron, silicon, or phosphorus.

4. The system of claim 1, wherein the first group of carbon quantum dots are dispersed in a first zone of the subterranean formation and the second group of carbon quantum dots are dispersed in a second zone of the subterranean formation.

5. The system of claim 1, wherein the first group of carbon quantum dots comprises carbon quantum dots having a different size than carbon quantum dots of the second group of carbon quantum dots.

6. The system of claim 1, wherein the first group of carbon quantum dots are formulated to fluoresce at a wavelength of about 450 nm and the second group of carbon quantum dots are formulated to fluoresce at a wavelength of about 700 nm.

7. The system of claim 1, wherein at least some of the carbon quantum dots include hydrophilic surfaces and at least some of the carbon quantum dots include hydrophobic surfaces.

8. A system for determining at least one property of at least one subterranean formation fluid, the system comprising:
   at least one fiber optic cable within a wellbore extending through at least one subterranean formation, the at least one fiber optic cable including at least one optical fiber comprising carbon quantum dots, the carbon quantum dots comprising a carbon core exhibiting at least one fluorescence property;
   a radiation source coupled to the at least one optical fiber, the radiation source configured to generate excitation radiation for transmission through the at least one optical fiber; and
   a detector coupled to the at least one fiber optic cable, the detector configured to measure the at least one fluorescence property of the carbon core.

9. The system of claim 8, wherein the carbon quantum dots are disposed within the at least one optical fiber.

10. The system of claim 8, wherein the at least one optical fiber comprises a coating of the carbon quantum dots on at least a portion thereof.

11. The system of claim 10, wherein the coating comprises a monolayer of the carbon quantum dots.

12. The system of claim 8, wherein the carbon quantum dots comprise a first group of undoped carbon quantum dots and at least a second group of carbon quantum dots doped with one or more of nitrogen, boron, silicon, or phosphorus.

13. The system of claim 8, further comprising at least another optical fiber coupled to the detector and configured to transmit emitted radiation from the carbon quantum dots to the detector.

14. The system of claim 8, wherein the carbon quantum dots comprise one or more of nitrogen, boron, silicon, or phosphorus.

15. The system of claim 8, wherein the detector is configured to measure at least one of an absorption spectrum, an emission spectrum, or a fluorescence intensity of the carbon quantum dots.

16. A method of forming carbon quantum dots, the method comprising:
   providing an electrolyte comprising a carbon source and a source of ions to an electrochemical cell;
   introducing the electrolyte between platinum electrodes of the electrochemical cell; and
   applying electrical current between the platinum electrodes and forming carbon quantum dots including carbon from the carbon source.

17. The method of claim 16, wherein providing an electrolyte comprising a carbon source comprises forming an electrolyte comprising one or more of ethanol and ethanolamine.

18. The method of claim 16, further comprising forming the electrolyte from one or more of an amino alcohol, a boron source, or a phosphorus source.

19. The method of claim 16, further comprising forming at least some carbon quantum dots comprising one of an amino alcohol, boron, silicon, or phosphorus and at least some carbon quantum dots comprising at least another of an amino alcohol, boron, or phosphorus.

20. The method of claim 16, further comprising forming hydrophilic surfaces on the carbon quantum dots or forming oleophilic surfaces on the carbon quantum dots.

* * * * *